US009345736B2

(12) United States Patent
Berry

(10) Patent No.: US 9,345,736 B2
(45) Date of Patent: May 24, 2016

(54) TOPICAL TREATMENT OF RADIATION DERMATITIS USING HAMELIA PATENS

(71) Applicant: BERRY PHARMACEUTICALS, L.L.C., Georgetown, TX (US)

(72) Inventor: Don Wayne Berry, Georgetown, TX (US)

(73) Assignee: BERRY PHARMACEUTICALS, L.L.C., Georgetown, TX (US)

( * ) Notice: Subject to any disclaimer, the term of this patent is extended or adjusted under 35 U.S.C. 154(b) by 0 days.

(21) Appl. No.: 13/815,957

(22) Filed: Mar. 16, 2013

(65) Prior Publication Data
US 2013/0251825 A1    Sep. 26, 2013

Related U.S. Application Data

(63) Continuation-in-part of application No. 12/661,567, filed on Mar. 19, 2010, now Pat. No. 8,652,534.

(60) Provisional application No. 61/272,641, filed on Oct. 14, 2009.

(51) Int. Cl.
| | | |
|---|---|---|
| *A61K 36/74* | (2006.01) | |
| *A61K 9/06* | (2006.01) | |
| *A61K 8/46* | (2006.01) | |
| *A61K 8/55* | (2006.01) | |
| *A61K 8/97* | (2006.01) | |
| *A61K 9/00* | (2006.01) | |
| *A61K 9/107* | (2006.01) | |
| *A61K 31/135* | (2006.01) | |
| *A61K 31/19* | (2006.01) | |
| *A61K 31/404* | (2006.01) | |
| *A61K 31/438* | (2006.01) | |
| *A61K 31/575* | (2006.01) | |
| *A61K 31/7048* | (2006.01) | |
| *A61Q 19/00* | (2006.01) | |

(52) U.S. Cl.
CPC . *A61K 36/74* (2013.01); *A61K 8/46* (2013.01); *A61K 8/553* (2013.01); *A61K 8/97* (2013.01); *A61K 9/0014* (2013.01); *A61K 9/0019* (2013.01); *A61K 9/06* (2013.01); *A61K 9/107* (2013.01); *A61K 31/135* (2013.01); *A61K 31/19* (2013.01); *A61K 31/404* (2013.01); *A61K 31/438* (2013.01); *A61K 31/575* (2013.01); *A61K 31/7048* (2013.01); *A61Q 19/004* (2013.01)

(58) Field of Classification Search
CPC .................. A61K 2300/00; A61K 36/185
USPC ........................................................ 424/725
See application file for complete search history.

(56) References Cited

U.S. PATENT DOCUMENTS

| | | | |
|---|---|---|---|
| 5,302,611 A | 4/1994 | Keplinger et al. | 514/411 |
| 5,498,420 A * | 3/1996 | Mentrup et al. | 424/450 |
| 5,869,060 A | 2/1999 | Yoon et al. | 424/195.1 |
| 6,063,770 A | 5/2000 | Falcon | 514/25 |
| 6,267,779 B1 * | 7/2001 | Gerdes | 607/89 |
| 7,105,529 B2 | 9/2006 | Davis et al. | 514/272 |
| 7,201,928 B1 | 4/2007 | Huang et al. | 424/736 |
| 7,273,625 B2 | 9/2007 | Lee | 424/725 |
| 2003/0103953 A1 | 6/2003 | Rosenbloom | 424/94.1 |
| 2007/0166255 A1 | 7/2007 | Gupta | 424/70.1 |
| 2011/0086088 A1* | 4/2011 | Berry | 424/450 |

FOREIGN PATENT DOCUMENTS

| | | |
|---|---|---|
| EP | 0933351 | 8/1999 |
| EP | 2060183 | 5/2009 |
| JP | 2002-020232 | 1/2002 |
| WO | WO 94/15902 | 7/1994 |
| WO | WO 2005/058255 | 6/2005 |
| WO | WO 2008/109717 | 9/2008 |

OTHER PUBLICATIONS

Seegenschmiedt et al., "Radiation Therapy for Nonmalignant Diseases in Germany: Current Concepts and Future Perspectives", 2004, Strahlentherapie und Onkologie, vol. 180, No. 11, pp. 718-730.*
Taylor, The Healing Power of Rainforest Herbs: A Guide to Understanding and Using Herbal Medicinals, 2005, Square One Publishers, pp. 144, 145, 417-420, and 505.*
Gomez-Beloz et al., "Double Incision Wound Healing Bioassay Using Hamelia Patens from El Salvador", 2003, Journal of Ethnopharmacology, vol. 88, pp. 169-173.*
Puglia et al., "Lipid nanoparticles for prolonged topical delivery: An in vitro and in vivo investigation", available online Feb. 3, 2008, International Journal of Pharmaceutics, vol. 357, pp. 295-304.*
Lee et al., "Effect of rosmarinic acid on atopic dermatitis", Dec. 30, 2008, Journal of Dermatology, vol. 35, pp. 768-771.*
Kumar et al., "Management of skin toxicity during radiation therapy: A review of the evidence", 2010, Journal of Medical Imaging and Radiation Oncology, vol. 54, pp. 264-279.*
*Carcinogenesis*, vol. 25, No. 4, pp. 549-557 (2004) Osakabe et al.
*Biosci. Biotechnol. Biochem*, 68(1) pp. 85-90 (2004) Banno et al.
*Chem. Pharm. Bull.* 54(5) pp. 561-564 (2005) Lim et al.
*Cancer Letters* 219 pp. 49-55 (2005) Fernandes et al.
*British Journal of Haemotology*, 132 pp. 615-622 (2005) Bacher et al.
*Phytomedicine* 14 pp. 280-284 (2007) Prado et al.
Ocampo, R. & Balick, M. "Plants of Semillas Sagradas: An Ethnobedicinal Garden in Costa Rica", 2009 Finca Luna Nueva Extractos de Costa Rica, ISBN 978-0-615-27415-7.
Sosa, S. et al. "Screening of the topical anti-inflammatory activity of some Central American plants", Medicinal & Armoatic Plants Abstracts, Scientific Publishers, New Delhi, India, vol. 24, No. 6, (2002); ISSN: 0250-4367.

(Continued)

*Primary Examiner* — Michael B Pallay
(74) *Attorney, Agent, or Firm* — Chris Whewell

(57) ABSTRACT

Topical compositions are provided useful for treating radiation dermatitis. The compositions comprise an extract of the plant *Hamelia patens* and are applied topically to skin having radiation dermatitis to relieve symptoms thereof.

20 Claims, No Drawings

(56) References Cited

OTHER PUBLICATIONS

Lopez Abraham et al. "*Extractos de plantas con propiedades citostaticas que crecen en Cuba*", Rev. Cub Med Trop 31: 2. 1979. English translation.

Pages 144, 145, 417-420, 505 from Scarlet bush, ED—Taylor L in "The Healing Power of Rainforest Herbs, Squareone"—Jan. 1, 2005 XP009152071.

Esposito-Avella et al. "*Pharmacological Screening of Panamanian Medicinal Plants, Part 1*" J. Crude Drug Res. 23 (1985) No. 1, pp. 17-25.

Einspahr, et al. "Chemoprevention of Human Skin Cancer" Clinical Reviews in Oncology Hematology, 41 (2002) 269-285. pp. 269-285.

List of chemical constituents of hamelia patens, from www.rain-tree.com/scarletbush.htm dated 2004 (6 pages).

www.cosmeticsdesign.com/Formulation-Science/New-ursolic-acid-ingredient-given-global-launch (2006) 6 pages.

www.ursolicacid.com/inhibition.htm, dated 2001 2 pages.

www.ursolicare.com, 7 pages.

Final rejection from parent case U.S. Appl. No. 12/661,567 dated Aug. 17, 2012.

Examiner's Answer to Appeal Brief in U.S. Appl. No. 12/661,567 dated Jan. 9, 2013.

List of chemical constituents of hamelia patens, from www.rain-tree.com, dated 2004 (2 pages).

www.cosmeticsdesign.com/Formulation-Science/New-ursolic-acid-ingredient-given-global-launch (2006) 3 pages.

www.ursolicare.com, 6 pages.

"Ionizing Radiation: The Good, the Bad, and the Ugly" Society for Investigative Dermatology vol. 132, pp. 985-993.

"Osteoradionecrosis of the Jaws" overview Oral Maxillofac. Surg (2010) vol. 14, pp. 3-16.

"Radiation Dermatitis: Clinical presentation, pathophysiology, and treatment 2006" J. Am. Acad. Dermatol. vol. 54, No. 1, pp. 28-46.

"Management of Skin Toxicity During Radiation Therapy: A Review of the Evidence" Journal of Medical Imaging and Radiation Oncology, 54 (2010) pp. 264-279.

"Dissecting the Molecular Mechanism of Ionizing Radiation-Induced Tissue Damage in the Feather Follicle" PLOS ONE, Feb. 2014 vol. 9, Issue 2 e89234, pp. 1-11.

"The Pathobiology of Mucositis" Nature Reviews, vol. 4, Apr. 2004, pp. 277-284.

Xu, et al. "A Review of Dosimetry Studies on External-beam Radiation Treatment With Respect to Second Cancer Induction" Phys. Med. Biol. 53 R193-R241, (2008).

Kirova, et al. "Second Malignancies After Breast Cancer: the Impact of Different Treatment Modalities" British Journal of Cancer, 98 870-874 (2008).

John B. Little "Radiation Carcinogenesis", Carcinogenesis, vol. 21, No. 3 397-404 (2000).

Jonathan W. Friedberg "Secondary Malignancies After Therapy of Indolent non-Hodgkins Lymphoma", Haemotological 93(3) pp. 336-338 (2008).

\* cited by examiner

TOPICAL TREATMENT OF RADIATION DERMATITIS USING HAMELIA PATENS

CROSS REFERENCE TO RELATED APPLICATIONS

This application is a Continuation-in-Part of U.S. patent application Ser. No. 12/661,567 filed Mar. 19, 2010, currently still pending, and claims the benefit of U.S. Provisional Application number 61/272,641 filed on Oct. 14, 2009, the entire contents of each of which are hereby incorporated herein by reference.

TECHNICAL FIELD

This invention relates generally to therapeutic, and other uses of compositions of matter, and to combinations including the compositions. In one narrower aspect, it relates to compositions useful for treating or preventing certain pre-cancerous and cancerous conditions. In another narrower aspect it relates to topical treatments for various skin-related ailments using compositions provided.

BACKGROUND OF THE INVENTION

Various compositions and materials have been proffered in the past as being beneficial in the treatment, alleviation, and prevention of various skin-related and other bodily disorders. One broad class of such materials are medicaments intended for topical use in the relief of symptoms of maladies such as basal cell carcinomae, actinic keratosis, and burns. Although there have been proposed many medicinal compositions and materials for treating a wide range of symptoms and conditions, few so far have proven efficacious and acceptable for alleviating the symptoms of, or causing remissions in solar keratosis lesions present on mammalian skin and in particular in reference to human skin.

Acute radiation dermatitis is known to include skin burns which are a non-malignant side effect of external beam irradiation therapy. Radiation dermatitis is mitigated with a view towards preventing the onset of the condition in the first place, reducing the severity of the skin reaction, and the reduction of healing time for instances in which it is manifest. There are few products or materials that successfully mitigate radiation dermatitis and other skin conditions arising from external beam irradiation therapy are available in the marketplace. Physicians have typically had to resort to attempt to treating the complication of radiation dermatitis with symptomatic and homeopathic applications that are limited in providing relief, resulting in a relatively low standard of care.

Cancer treatments using external beam irradiation are well known in the art to be the source of skin burns, particularly when an erythema-causing dose typically on the order of about 1.8 to 2.2 Gray (Gy) daily for multiple days of ionizing radiation is applied to mammalian skin, the erythemas presenting as red papules sometimes accompanied by desquamation or blistering. Radiation employed in external beam irradiation is often derived from radioisotopes of elements selected from the group consisting of: cobalt, cesium, iodine, platinum, and yttrium and is often a beta particle. Standardized doses of particle emissions from decay of the selected radioisotope are subsequently acted upon by a particle accelerator towards the target at the time of therapy. Radiation employed in external beam irradiation is also known to comprise irradiation of mammalian skin using photons, including infrared, visible, and ultraviolet light photons.

In general, when external beam irradiation is to be employed, dosage treatment planning is done on an individual basis according to established patterns derived from clinical trials for specific conditions and diagnoses. In addition, calculated dosage varies dependently on the site of treatment. For example in some known treatment regimens for head and neck areas, the amount of radiation employed is on the order of about 70 Gy. In some known treatment regimens for breast areas the amount of radiation employed is on the order of about 50-60 Gy. In some known treatment regimens for gastrointestinal tract areas the amount of radiation employed is on the order of about 48 Gy. In some known treatment regimens employing external beam irradiation, standardized dosage patterns are from about 1.8 to 2.2 Gy per day using fewer than 35 different treatment sessions, typically using dose fraction schedules with fractionation for known and acceptable doses being industry-standardized. In some known treatment regimens employing external beam irradiation, a single frequency of radiation is used, whereas in other regimens a plurality of frequencies are simultaneously administered to the subject.

SUMMARY OF THE INVENTION

Methods are provided for alleviating symptoms induced by external beam irradiation on a mammalian subject. A method according to some embodiments comprises contacting a composition containing a *hamelia patens* extract to the skin of a mammalian subject in an effective amount and frequency for reducing symptoms from burns having resulted from a clinical exposure of external beam irradiation therapy.

Compositions used in some embodiments of alleviating symptoms induced by external beam irradiation comprise a pharmaceutically-acceptable carrier in combination with at least one material selected from the group consisting of: an alkaloid, pigenin-7-o-beta d-glucuronide; aricine; catequine; 24-methylenecycloartane-3β-ol; 24-methylcycloart-24-en-3β-ol; 2 E-3,7,11,15,19-pentamethyl-2-eicosane-1-ol; ephedrine; flavonones; 2'-5-5'-7-tetrahydroxy-7-o-rutinoside; isomaruquine; isopteropodine; maruquine; the methyl ester of maruquine; narirutin; narirutin (2r); narirutin (2s); oxindole alkaloids; oxindole aricine; palmirine; pteropodine; rumberine; rosmarinic acid; rotundic acid; rumberine; rutin; seneciophylline; β-sitosterol; speciophylline; stigmast-4-en-3-3-dione; stigmast-4-en-3-6-dione; stigmasterol; tannins; and ursolic acid, and including any mixtures thereof, present in an effective amount for alleviating symptoms of said disorder.

DETAILED DESCRIPTION

This disclosure concerns the plant known as *hamelia patens*, its parts, their constituents, and extracts or concentrates prepared therefrom, as well as certain particular therapeutic effects relating thereto. *Hamelia patens* is a perennial shrub or shrub-like plant that is sometimes referred to as Scarlet Bush, Firebush, and Texas Firecracker, among other common names. *Hamelia patens* grows in Florida, Texas, and other southern and southwestern states, and is also distributed throughout central and south America. The plant has a woody stem and roots, broad leaves and at maturity produces bright red berries. An extract provided in accordance with this disclosure is produced using any combination of parts of the *hamelia patens* plant, of any of its species, which parts are selected from the group consisting of: its roots, stems, leaves, and fruit.

A *hamelia patens* extract in some embodiments according to this disclosure is provided by first picking leaves from a species of the plant, the species in one non-limiting embodiment being *hamelia patens* jacq. In one embodiment about 509 grams of freshly-picked leaves of *Hamelia Patens* Jacq. were procured from *hamelia patens* jacq. grown in Texas. Stems were removed from the leaves and the leafy material was cut transversely into strips. The cut leafy material was combined with about 475 milliliters of CETAPHIL® gentle skin cleanser (Galderma Laboratories) in a covered one-liter beaker and blended using a stirring rod until the leafy material was evenly distributed throughout the bulk of the composition. The contents of the beaker were heated to 65.5 degrees centigrade for 30 minutes with frequent stirring. During the course of the heating the leaves turned to a dull green with a brown cast. At the end of the 30 minutes the leafy material was compacted using a potato masher, to squeeze more of the plant-borne matter from the leaves and into the bulk of the composition. Finally, the beaker's contents were poured through a stainless steel screen, of sufficient mesh to separate the solid matter including leaves from the liquid portion, which liquid portion itself was subsequently strained through cheesecloth, thus providing a liquid *hamelia patens* extract according to one embodiment of the disclosure.

In other embodiments of providing a *hamelia patens* extract, a protic solvent such as water, or a lower alcohol, or a mixture comprising a plurality of lower alcohols, or blends comprising one or a plurality of lower alcohols and water, when miscible, in any relative proportions, is employed as a liquid solvent into which the plants' constituents are extracted. In some embodiments the lower alcohol is any alcohol selected from any C1-C4 alcohol, including any mixtures thereof, independently present in any proportion. In some embodiments a water/alcohol mixture containing any amount in the range from about 5% to about 10% by volume of the alcohol in water is used as a solvent. Various extraction techniques known in the art may be employed, including percolation, soxhlet, and other extraction techniques, including those employing supercritical carbon dioxide. In one embodiment about 500 grams of ground *hamelia patens* leaves are combined with about 500 ml of a mixture that is 10% by volume of ethanol and 90% by volume of water, and heated to about 65 degrees centigrade for 30 minutes. In alternate embodiments, the solvent is maintained at room temperature and the mixture of plant matter and solvent is permitted to percolate for an extended time, of up to about 24 hours. In other embodiments, a longer extraction time in the range of between about 24 hours and about 72 hours is employed. The resulting solution from such heating, percolation, or other extraction technique is centrifuged (optionally) and filtered to provide a liquid solution *hamelia patens* extract. This solution extract is in one embodiment applied as-is to mammalian skin. In alternate embodiments various other materials may be combined with such solution extract to form skin creams, etc., as described below prior to its application to mammalian skin. In some embodiments, the solvent present in such a liquid solution extract is removed using techniques known to those skilled in the art (including reduced pressure distillation, flash evaporation, etc.) to yield a crystalline extract in the form of a dry powder. In some embodiments, the temperature of the liquid solvent extract is not permitted to exceed about 50 degrees centigrade during solvent removal. In one embodiment when a solvent comprising 10% by volume ethanol in 90% by volume water is employed at room temperature in a percolation lasting about 24 hours, the yield of dry crystalline *hamelia patens* extract provided following solvent removal amounts to about 7% by weight based on the weight of the fresh-cut *hamelia patens* leaves employed. Typically by such processing the yield of crystalline *hamelia patens* extract ranges from between about 2% to about 8% by weight based on the weight of the plant matter used. While crystalline extracts are mentioned herein, it is understood by those skilled in the art that extracts obtained following solvent removal may not always be crystalline or powdered crystalline in nature owing to variation among individual plants' growing condition, time of harvest, and genetics, which can impact polymeric residues present. Thus in some embodiments a non-completely-crystalline residue may be obtained, such as partially-gummy residues; however in general such non-completely crystalline extracts obtained are substantially functionally-equivalent to a crystalline extract and are to be treated herein as being synonymous therewith for purposes of this specification and claims appended hereto.

From dry powdered crystalline extract(s), compositions according to the disclosure are prepared by mixing such extract(s) with various other materials, as desired. In some embodiments the crystalline *hamelia patens* extract is ground with a mortar or otherwise pulverized and combined with or formulated into a skin crème or skin lotion at any desired concentration, which concentration of crystalline *hamelia patens* extract is between about 0.05% by weight and about 85% by weight based on the weight of the final composition, including all weight percentages and ranges of weight percentages therebetween. In some embodiments the crystalline *hamelia patens* extract is blended with at least one other material that is a solid or liquid at room temperature, in any amount, in order to provide an extract concentrate. Such at least one other material in some embodiments comprises a material selected from the group consisting of: silicates, aluminosilicates and silica present in effective flow-enhancing amounts to enable the crystalline extract to flow freely when poured. In other embodiments, a crystalline *hamelia patens* extract according to the disclosure is combined with a solvent, to provide a solution that comprises an extract concentrate, in any amount between about 1% by weight based on the total weight of the concentrate, up to the saturation limit of the crystalline extract in the solvent employed at ambient temperatures.

In some embodiments a crystalline *hamelia patens* extract so obtained is combined with a glyceryl ester based oil that is plant-derived, and in some embodiments with a mixture of such glyceryl ester based oils. Suitable glyceryl ester based oils include without limitation oils such as soybean oil, coconut oil, palm oil, corn oil, olive oil, sunflower oil, safflower oil, cottonseed oil, rape oil, almond oil, sesame oil, peanut oil, and mixtures thereof in any proportion. A composition according to some embodiments of this disclosure includes the crystalline *hamelia patens* extract in combination with a plant-derived oil (alternately mixtures including a plurality of such oils, each present in any proportion), wherein the crystalline extract of *hamelia patens* is present in any amount between about 0.05% by weight to about 85% by weight, based on the total weight of the composition, including all percentages by weight and ranges of percentages by weight therebetween. The presence of a fatty acid ester type oil as a vehicle in general is capable of facilitating transdermal passage of at least one component material present in *hamelia patens* extract into and through mammalian skin. As used in this disclosure, mammalian skin includes human skin, and mammalian subjects include human subjects.

In other embodiments, the crystalline *hamelia patens* extract is combined with water or a water/alcohol mixture as described above to provide further compositions according to the disclosure. Compositions according to some embodiments of the disclosure include a crystalline *hamelia patens* extract in combination with water, and in alternate embodiments in combination with water/alcohol mixtures, and in these aqueous and aqueous alcohol embodiments the crystalline *hamelia patens* extract is present in any amount between about 0.05% by weight and about 85% by weight, based on the total weight of the composition, including all percentages by weight and ranges of percentages by weight therebetween. In different embodiments any C1 to C4 alcohol (including any mixtures thereof in any proportion) are used, either mixed with water in any chosen proportion, or substantially anhydrous.

In another embodiment, about a one-liter volume of cut *hamelia patens* leaves are compressed and combined with about 125 ml of petrolatum, the mixture being heated to any temperature in the range of between about sixty (60) degrees centigrade and about eighty (80) degrees centigrade for about 10 minutes. This provides a hydrocarbon base containing *hamelia patens* extract that is in some embodiments able to be applied directly to mammalian skin, or alternately is useful in preparing compositions according to other embodiments of this disclosure. In one embodiment this petrolatum-borne extract is combined with effective amounts of one (and alternately any number more than one) of an anti-inflammatory, anti-oxidant, and/or anti-bacterial material to provide an enhanced *hamelia patens* extract. Such a petrolatum-borne *hamelia patens* extract is easy to handle enabling quick and ready blending with other materials. In addition, petrolatum itself is not absorbed by the skin. In other embodiments, the powdered crystalline *hamelia patens* extract referred to above is combined with petrolatum and heated with agitation to provide a composition according to the disclosure wherein the crystalline extract of *hamelia patens* is present in any amount between about 0.05% by weight to about 85% by weight, based on the total weight of the petrolatum-based composition, including all percentages by weight and ranges of percentages by weight therebetween.

In another embodiment, a liquid solution *hamelia patens* extract, (for example prepared by combining *hamelia patens* plant parts with a solvent and percolating at about 60 degrees centigrade) wherein the solvent is a 90% water/10% ethanol (by volume) mixture is combined with any vegetable oil to provide a mixture that is heated with stirring sufficiently to simmer off the water and alcohol present, causing the *hamelia patens* extract to be taken up into the oil. For such embodiments, the quantity of water/ethanol extract and oil used are selected to provide an amount of crystalline *hamelia patens* extract present in the final composition in any amount between about 0.05% by weight and about 85% by weight, based on the total weight of the composition, including all percentages by weight and ranges of percentages by weight therebetween. In alternate embodiments, one begins with the crystalline *hamelia patens* extract and dissolves it in water/ethanol mixture comprising about 10% ethanol by volume and once dissolved, this mixture is combined with any desired amount of oil, the water/ethanol present is subsequently simmered off by heating to afford an oil-borne *hamelia patens* extract.

Thus, the present disclosure in some embodiments provides compositions comprising a crystalline *hamelia patens* extract in combination with at least one material selected from the group consisting of: water, water/alcohol mixtures, hydrocarbons (petrolatum) and ester-type fats or oils, wherein the *hamelia patens* extract is present in any amount between about 0.05% by weight to about 85% by weight, based on the total weight of the composition, including all percentages by weight and ranges of percentages by weight therebetween.

Crystalline or liquid (including aqueous, non-aqueous, alcoholic, hydrocarbon-based, and oil-borne) *hamelia patens* extracts as provided herein may be further refined to isolate or concentrate any one, or more than one, of the compounds present in *hamelia patens* using methods or techniques generally known to those skilled in the art.

A *hamelia patens* extract provided according to some embodiments of the disclosure contains at least any one compound, and in other embodiments contains any mixture comprising a plurality including any two or more than two compounds present in the listing now set forth, the compounds in such listing comprising: alkaloids, 2-alpha-hydroxyursolic acid, apigenin-7-o-beta d-glucuronide, aricine, catequine, 19-alphahydroxy Asiatic acid, 24-methylenecycloartane-3β-ol, 24-methylcycloart-24-en-3β-ol, 2 E-3,7,11,15,19-pentamethyl-2-eicosane-1-ol, ephedrine, flavonones, 2'-5-5'-7-tetrahydroxy-7-o-rutinoside, isomaruquine, isopteropodine, maruquine, the methyl ester of maruquine, mitraphylline, narirutin, narirutin (2r), narirutin (2s), oxindole alkaloids, oxindole aricine, palmirine, pigenin-7-o-beta D-glucuronide, pomolic acid, pteropodine, rumberine, rosmarinic acid, rotundic acid, rumberine, rutin, seneciophylline, β-sitosterol, speciophylline, stigmast-4-en-3-3-dione, stigmast-4-en-3-6-dione, stigmasterol, tannins, tormentic acid, uncarine F, and ursolic acid. In some embodiments, all of these compounds are present in a *hamelia patens* extract useful for providing a composition according to this disclosure.

Accordingly, a *hamelia patens* extract as provided in some embodiments contains alkaloids. In some embodiments alkaloids are present in a composition according to the disclosure in any amount between about 0.05% and about 30% by weight based on the total weight of the composition, including all weight percents and ranges of weight percents therebetween. A *hamelia patens* extract as provided in some embodiments contains apigenin-7-o-beta d-glucuronide. In some embodiments apigenin-7-o-beta d-glucuronide is present in a composition according to the disclosure in any amount between about 0.05% and about 30% by weight based on the total weight of the composition, including all weight percents and ranges of weight percents therebetween. A *hamelia patens* extract as provided in some embodiments contains aricine. In some embodiments aricene is present in a composition according to the disclosure in any amount between about 0.05% and about 30% by weight based on the total weight of the composition, including all weight percents and ranges of weight percents therebetween. A *hamelia patens* extract as provided in some embodiments contains catequine. In some embodiments catequine is present in a composition according to the disclosure in any amount between about 0.05% and about 30% by weight based on the total weight of the composition, including all weight percents and ranges of weight percents therebetween. A *hamelia patens* extract as provided in some embodiments contains 24-methylenecycloartane-3β-ol. In some embodiments 24-methylenecycloartane-3β-ol is present in a composition according to the disclosure in any amount between about 0.05% and about 30% by weight based on the total weight of the composition, including all weight percents and ranges of weight percents therebetween. A *hamelia patens* extract as provided in some embodiments contains 24-methylcycloart-24-en-3β-ol. In some embodiments 24-methylcycloart-24-en-3β-ol is present in a composition according to the disclosure in any amount between about 0.05% and about 30% by weight based on the total weight of the composition, including all weight percents and ranges of weight percents therebetween. A *hamelia patens* extract as provided in some embodiments contains 2 E-3,7,11,15,19-pentamethyl-2-eicosane-1-ol. In some embodiments 2 E-3,7,11,15,19-pentamethyl-2-eicosane-1-ol is present in a composition according to the disclosure in any amount between about 0.05% and about 30% by weight based on the total weight of the composition, including all weight percents and ranges of weight percents therebetween. A *hamelia patens* extract as provided in some embodiments contains ephedrine. In some embodiments ephedrine is present in a composition according to the disclosure in any amount between about 0.05% and about 30% by weight based on the total weight of the composition, including all weight percents and ranges of weight percents therebetween. A *hamelia patens* extract as provided in some embodiments contains flavonones. In some embodiments flavonones are present in a composition according to the disclosure in any amount between about 0.05% and about 30% by weight based on the total weight of the composition, including all weight percents and ranges of weight percents therebetween. A *hamelia patens* extract as provided in some embodiments contains 2'-5-5'-7-tetrahydroxy-7-o-rutinoside. In some embodiments 2'-5-5'-7-tetrahydroxy-7-o-rutinoside is present in a composition according to the disclosure in any amount between about 0.05% and about 30% by weight based on the total weight of the composition, including all weight percents and ranges of weight percents therebetween. A *hamelia patens* extract as provided in some embodiments contains 19-alpha-hydroxy asiatic acid. In some embodiments 19-alpha-hydroxy asiatic acid is present in a composition according to the disclosure in any amount between about 0.05% and about 30% by weight based on the total weight of the composition, including all weight percents and ranges of weight percents therebetween. A *hamelia patens* extract as provided in some embodiments contains isomaruquine. In some embodiments isomaruquine is present in a composition according to the disclosure in any amount between about 0.05% and about 30% by weight based on the total weight of the composition, including all weight percents and ranges of weight percents therebetween. A *hamelia patens* extract as provided in some embodiments contains isopteropodine. In some embodiments isopteropodine is present in a composition according to the disclosure in any amount between about 0.05% and about 30% by weight based on the total weight of the composition, including all weight percents and ranges of weight percents therebetween. A *hamelia patens* extract as provided in some embodiments contains maruquine. In some embodiments maruquine is present in a composition according to the disclosure in any amount between about 0.05% and about 30% by weight based on the total weight of the composition, including all weight percents and ranges of weight percents therebetween. A *hamelia patens* extract as provided in some embodiments contains the methyl ester of maruquine. In some embodiments the methyl ester of maruquine is present in a composition according to the disclosure in any amount between about 0.05% and about 30% by weight based on the total weight of the composition, including all weight percents and ranges of weight percents therebetween. A *hamelia patens* extract as provided in some embodiments contains mitraphylline. In some embodiments mitraphylline is present in a composition according to the disclosure in any amount between about 0.05% and about 30% by weight based on the total weight of the composition, including all weight percents and ranges of weight percents therebetween. A *hamelia patens* extract as provided in some embodiments contains narirutin. In some embodiments narirutin is present in a composition according to the disclosure in any amount between about 0.05% and about 30% by weight based on the total weight of the composition, including all weight percents and ranges of weight percents therebetween. A *hamelia patens* extract as provided in some embodiments contains narirutin (2r). In some embodiments narirutin (2r) is present in a composition according to the disclosure in any amount between about 0.05% and about 30% by weight based on the total weight of the composition, including all weight percents and ranges of weight percents therebetween. A *hamelia patens* extract as provided in some embodiments contains narirutin (2s). In some embodiments narirutin (2s) is present in a composition according to the disclosure in any amount between about 0.05% and about 30% by weight based on the total weight of the composition, including all weight percents and ranges of weight percents therebetween. A *hamelia patens* extract as provided in some embodiments contains oxindole alkaloids. In some embodiments oxindole alkaloids are present in a composition according to the disclosure in any amount between about 0.05% and about 30% by weight based on the total weight of the composition, including all weight percents and ranges of weight percents therebetween. A *hamelia patens* extract as provided in some embodiments contains oxindole In some embodiments oxindole aricine is present in a composition according to the disclosure in any amount between about 0.05% and about 30% by weight based on the total weight of the composition, including all weight percents and ranges of weight percents therebetween. A *hamelia patens* extract as provided in some embodiments contains palmirine. In some embodiments palmirine is present in a composition according to the disclosure in any amount between about 0.05% and about 30% by weight based on the total weight of the composition, including all weight percents and ranges of weight percents therebetween. A *hamelia patens* extract as provided in some embodiments contains pigenin-7-o-beta D-glucuronide. In some embodiments pigenin-7-o-beta D-glucuronide is present in a composition according to the disclosure in any amount between about 0.05% and about 30% by weight based on the total weight of the composition, including all weight percents and ranges of weight percents therebetween. A *hamelia patens* extract as provided in some embodiments contains pomolic acid. In some embodiments pomolic acid is present in a composition according to the disclosure in any amount between about 0.05% and about 30% by weight based on the total weight of the composition, including all weight percents and ranges of weight percents therebetween. A *hamelia patens* extract as provided in some embodiments contains pteropodine. In some embodiments pteropodine is present in a composition according to the disclosure in any amount between about 0.05% and about 30% by weight based on the total weight of the composition, including all weight percents and ranges of weight percents therebetween. A *hamelia patens* extract as provided in some embodiments contains rumberine. In some embodiments rumberine is present in a composition according to the disclosure in any amount between about 0.05% and about 30% by weight based on the total weight of the composition, including all weight percents and ranges of weight percents therebetween. A *hamelia patens* extract as provided in some embodiments contains rosmarinic acid. In some embodiments rosmarinic acid is present in a composition according to the disclosure in any amount between about 0.05% and about 30% by weight based on the total weight of the composition, including all weight percents and ranges of weight percents therebetween. A *hamelia patens* extract as provided in some embodiments contains rotundic acid. In some embodiments rotundic acid is present in a composition according to the disclosure in any amount between about 0.05% and about 30% by weight based on the total weight of the composition, including all weight percents and ranges of weight percents therebetween. A *hamelia patens* extract as provided in some embodiments contains rumberine. In some embodiments rumberine is present in a composition according to the disclosure in any amount between about 0.05% and about 30% by weight based on the total weight of the composition, including all weight percents and ranges of weight percents therebetween. A *hamelia patens* extract as provided in some embodiments contains rutin. In some embodiments rutin is present in a composition according to the disclosure in any amount between about 0.05% and about 30% by weight based on the total weight of the composition, including all weight percents and ranges of weight percents therebetween. A *hamelia patens* extract as provided in some embodiments contains seneciophylline. In some embodiments seneciophylline is present in a composition according to the disclosure in any amount between about 0.05% and about 30% by weight based on the total weight of the composition, including all weight percents and ranges of weight percents therebetween. A *hamelia patens* extract as provided in some embodiments contains β-sitosterol. In some embodiments β-sitosterol is present in a composition according to the disclosure in any amount between about 0.05% and about 30% by weight based on the total weight of the composition, including all weight percents and ranges of weight percents therebetween. A *hamelia patens* extract as provided in some embodiments contains speciophylline. In some embodiments speciophylline is present in a composition according to the disclosure in any amount between about 0.05% and about 30% by weight based on the total weight of the composition, including all weight percents and ranges of weight percents therebetween. A *hamelia patens* extract as provided in some embodiments contains stigmast-4-en-3-3-dione. In some embodiments stigmast-4-en-3-3-dione is present in a composition according to the disclosure in any amount between about 0.05% and about 30% by weight based on the total weight of the composition, including all weight percents and ranges of weight percents therebetween. A *hamelia patens* extract as provided in some embodiments contains stigmast-4-en-3-6-dione. In some embodiments stigmast-4-en-3-6-dione is present in a composition according to the disclosure in any amount between about 0.05% and about 30% by weight based on the total weight of the composition, including all weight percents and ranges of weight percents therebetween. A *hamelia patens* extract as provided in some embodiments contains stigmasterol. In some embodiments stigmasterol is present in a composition according to the disclosure in any amount between about 0.05% and about 30% by weight based on the total weight of the composition, including all weight percents and ranges of weight percents therebetween. A *hamelia patens* extract as provided in some embodiments contains tannins. In some embodiments tannins are present in a composition according to the disclosure in any amount between about 0.05% and about 30% by weight based on the total weight of the composition, including all weight percents and ranges of weight percents therebetween. A *hamelia patens* extract as provided in some embodiments contains tormentic acid. In some embodiments tormentic acid is present in a composition according to the disclosure in any amount between about 0.05% and about 30% by weight based on the total weight of the composition, including all weight percents and ranges of weight percents therebetween. A *hamelia patens* extract as provided in some embodiments contains uncarine F. In some embodiments uncarine F is present in a composition according to the disclosure in any amount between about 0.05% and about 30% by weight based on the total weight of the composition, including all weight percents and ranges of weight percents therebetween. A *hamelia patens* extract as provided in some embodiments contains ursolic acid. In some embodiments ursolic acid is present in a composition according to the disclosure in any amount between about 0.05% and about 30% by weight based on the total weight of the composition, including all weight percents and ranges of weight percents therebetween. A *hamelia patens* extract as provided in some embodiments contains 2-alpha-hydroxy ursolic acid. In some embodiments 2-alpha-hydroxy ursolic acid is present in a composition according to the disclosure in any amount between about 0.05% and about 30% by weight based on the total weight of the composition, including all weight percents and ranges of weight percents therebetween. Terms including "about" when used herein, such as "about 30%", are understood as also including the exact numerical value occurring immediately subsequent to "about", in the same context, i.e., such a recitation as "about 30%" includes the exact value specified, in this instance exactly 30%. In some embodiments, each of the component materials in the listing above, when present in a *hamelia patens* extract, are present in amounts within their specified ranges independently with respect to the amounts of the other components present.

As concerns any one or more than one of the foregoing materials in said listing which are described as being acids, the present disclosure includes the presence of such materials in their neutralized forms, and in alternate embodiments their esterified forms condensed with any alcohol or polyol. For those component compounds in the listing having a carboxylic acids function, the present disclosure includes the presence of such materials in their anionic forms, including without limitation their alkali metal salts, alkaline earth salts, ammonium salts and substituted ammonium salts, the concentration of the anionic forms of such material(s) being present in a composition according to the disclosure in the amounts specified for the acid form of the material(s). In some embodiments the concentration ranges for components present in a composition according to the disclosure are applied based on the weight percent of the anionic form of the material. In some embodiments, the concentration ranges in a composition according to the disclosure are determined based on the weight percent of the salt, including the cation present. Likewise when basic substances are recited, the present disclosure includes the presence of such materials in their protonated forms, the concentration ranges of such materials being present in a composition according to the disclosure in the amounts specified above for the basic form. In some embodiments the concentration ranges for a composition according to the disclosure is determined based on the weight percent of the protonated form of the material present. In some embodiments, the concentration ranges for a composition according to the disclosure is determined based on the weight percent of the protonated form of the material and including its anion present for charge neutrality present.

In some embodiments, all of the materials in the above listing are present in a composition according to the disclosure. In other embodiments any one or more than one of the materials in the above listing are independently be omitted from the contents of a composition according to the disclosure, such as by refining a *hamelia patens* extract (including a crystalline *hamelia patens* extract) for the purpose of removal of one, or any number greater than one, of materials in the above listing present in the extract using techniques known to those skilled in the art. In other embodiments any one or any number greater than one of such components present in the listing may be purified using techniques known to those of ordinary skill in the art. For example, to remove nitrogenous bases the extract material is put up into aqueous solution and made alkaline, and extraction done using CHCl3 to remove amino compounds, the aqueous layer being subsequently re-acidified or neutralized. In one embodiment, ammonia is used to make the material alkaline for purposes of such extraction, which ammonia is subsequently removed after the extraction having been completed by blowing with nitrogen or treatment to reduced pressure. In another embodiment an aqueous extract of *hamelia patens* is made slightly acidic by addition of HCl, and extractions are done using ethyl acetate, ether, chloroform, and/or hexanes. Following extraction, the aqueous layer is subjected to reduced pressure and slight heating or a sweep of nitrogen or other inert gas to facilitate removal of the HCl. In such embodiments, fractions obtained may be further treated to selectively separate or remove component materials present, using techniques known in the art including without limitation such techniques as preparatory chromatography columns, fractional distillation under vacuo, molecular distillation, precipitation and filtration, etc. In further embodiments, one or more than one of any of the above-named components in the listing are produced synthetically or are otherwise acquired or produced, and are subsequently blended with one another to provide a blend that comprises a synthetic *hamelia patens* extract that is useful in providing a composition according to the disclosure, such components that are selected to be present each being individually present at levels within the ranges specified herein.

An extract of the plant *hamelia patens* according to some embodiments of the disclosure may thus comprise a crude (water-based, H2O/alcohol based, oil-based, or petrolatum based) *hamelia patens* extract from which any one, or any combination including any number more than one of, the component materials set forth in the listing above are omitted or removed from said extract, the resulting extract being useful for providing a composition according to this disclosure. In some embodiments at least any chosen two of the component materials selected from the group consisting of the materials recited in the listing above remain or are present in a *hamelia patens* extract useful for providing a composition according to this disclosure, the component materials being independently present at concentrations within any of the ranges specified above in such compositions or extracts. In some embodiments at least any chosen three of the component materials selected from the group consisting of the materials recited in the listing above remain or are present in a *hamelia patens* extract useful for providing a composition according to this disclosure, the component materials being independently present at concentrations within the ranges specified above in such compositions or extracts. In some embodiments at least any chosen four of the component materials selected from the group consisting of the materials recited in the listing above remain or are present in a *hamelia patens* extract useful for providing a composition according to this disclosure, the component materials being independently present at concentrations within the ranges specified above in such composition or extracts. In some embodiments at least any chosen five of the component materials selected from the group consisting of the materials recited in the listing above remain or are present in a *hamelia patens* extract useful for providing a composition according to this disclosure, the component materials being independently present at concentrations within the ranges specified above in such compositions or extracts.

This disclosure includes *hamelia patens* extracts from which some of the components in the listing above have been removed, and also *hamelia patens* extracts comprising a plurality of the materials in the listing above which are produced by combining previously-isolated purified component materials from such listing. In some embodiments, all alkaloids are omitted or removed when providing a *hamelia patens* extract according to the disclosure, the remaining components of the listing remaining present. In some embodiments, all 2-alpha-hydroxyursolic acid is omitted or removed when providing a *hamelia patens* extract according to the disclosure, the remaining components of the listing remaining present. In some embodiments, all flavonones are omitted or removed when providing a *hamelia patens* extract according to the disclosure, the remaining components of the listing remaining present. In some embodiments, all apigenin-7-o-beta d-glucuronide is omitted or removed when providing a *hamelia patens* extract according to the disclosure, the remaining components of the listing remaining present. In some embodiments, all aricine is omitted or removed when providing a *hamelia patens* extract according to the disclosure, the remaining components of the listing remaining present. In some embodiments, all catequine is omitted or removed when providing a *hamelia patens* extract according to the disclosure, the remaining components of the listing remaining present. In some embodiments, all flavonones is omitted or removed when providing a *hamelia patens* extract according to the disclosure, the remaining components of the listing remaining present. In some embodiments, all 19-alphahydroxy Asiatic acid is omitted or removed when providing a *hamelia patens* extract according to the disclosure, the remaining components of the listing remaining present. In some embodiments, all 24-methylenecycloartane-3$\beta$-ol is omitted or removed when providing a *hamelia patens* extract according to the disclosure, the remaining components of the listing remaining present. In some embodiments, all 24-methylcycloart-24-en-3$\beta$-ol is omitted or removed when providing a *hamelia patens* extract according to the disclosure, the remaining components of the listing remaining present. In some embodiments, all 2 E-3,7,11,15,19-pentamethyl-2-eicosane-1-ol is omitted or removed when providing a *hamelia patens* extract according to the disclosure, the remaining components of the listing remaining present. In some embodiments, all ephedrine is omitted or removed when providing a *hamelia patens* extract according to the disclosure, the remaining components of the listing remaining present. In some embodiments, all 2'-5-5'-7-tetrahydroxy-7-o-rutinoside is omitted or removed when providing a *hamelia patens* extract according to the disclosure, the remaining components of the listing remaining present. In some embodiments, all flavonones are omitted or removed when providing a *hamelia patens* extract according to the disclosure, the remaining components of the listing remaining present. In some embodiments, all isomaruquine is omitted or removed when providing a *hamelia patens* extract according to the disclosure, the remaining components of the listing remaining present. In some embodiments, all isopteropodine is omitted or removed when providing a *hamelia patens* extract according to the disclosure, the remaining components of the listing remaining present. In some embodiments, all maruquine is omitted or removed when providing a *hamelia patens* extract according to the disclosure, the remaining components of the listing remaining present. In some embodiments, all the methyl ester of maruquine is omitted or removed when providing a *hamelia patens* extract according to the disclosure, the remaining components of the listing remaining present. In some embodiments, all mitraphylline is omitted or removed when providing a *hamelia patens* extract according to the disclosure, the remaining components of the listing remaining present. In some embodiments, all narirutin is omitted or removed when providing a *hamelia patens* extract according to the disclosure, the remaining components of the listing remaining present. In some embodiments, all narirutin (2r) is omitted or removed when providing a *hamelia patens* extract according to the disclosure, the remaining components of the listing remaining present. In some embodiments, all narirutin (2s) is omitted or removed when providing a *hamelia patens* extract according to the disclosure, the remaining components of the listing remaining present. In some embodiments, all oxindole alkaloids are omitted or removed when providing a *hamelia patens* extract according to the disclosure, the remaining components of the listing remaining present. In some embodiments, all oxindole aricine is omitted or removed when providing a *hamelia patens* extract according to the disclosure, the remaining components of the listing remaining present. In some embodiments, all palmirine is omitted or removed when providing a *hamelia patens* extract according to the disclosure, the remaining components of the listing remaining present. In some embodiments, all pigenin-7-o-beta D-glucuronide is omitted or removed when providing a *hamelia patens* extract according to the disclosure, the remaining components of the listing remaining present. In some embodiments, all pomolic acid is omitted or removed when providing a *hamelia patens* extract according to the disclosure, the remaining components of the listing remaining present. In some embodiments, all pteropodine is omitted or removed when providing a *hamelia patens* extract according to the disclosure, the remaining components of the listing remaining present. In some embodiments, all rumberine is omitted or removed when providing a *hamelia patens* extract according to the disclosure, the remaining components of the listing remaining present. In some embodiments, all rosmarinic acid is omitted or removed when providing a *hamelia patens* extract according to the disclosure, the remaining components of the listing remaining present. In some embodiments, all rotundic acid is omitted or removed when providing a *hamelia patens* extract according to the disclosure, the remaining components of the listing remaining present. In some embodiments, all rutin is omitted or removed when providing a *hamelia patens* extract according to the disclosure, the remaining components of the listing remaining present. In some embodiments, all seneciophylline is omitted or removed when providing a *hamelia patens* extract according to the disclosure, the remaining components of the listing remaining present. In some embodiments, all β-sitosterol is omitted or removed when providing a *hamelia patens* extract according to the disclosure, the remaining components of the listing remaining present. In some embodiments, all speciophylline is omitted or removed when providing a *hamelia patens* extract according to the disclosure, the remaining components of the listing remaining present. In some embodiments, all stigmast-4-en-3-3-dione is omitted or removed when providing a *hamelia patens* extract according to the disclosure, the remaining components of the listing remaining present. In some embodiments, all stigmast-4-en-3-6-dione is omitted or removed when providing a *hamelia patens* extract according to the disclosure, the remaining components of the listing remaining present. In some embodiments, all stigmasterol is omitted or removed when providing a *hamelia patens* extract according to the disclosure, the remaining components of the listing remaining present. In some embodiments, all tannins are omitted or removed when providing a *hamelia patens* extract according to the disclosure, the remaining components of the listing remaining present. In some embodiments, all tormentic acid is omitted or removed when providing a *hamelia patens* extract according to the disclosure, the remaining components of the listing remaining present. In some embodiments, all uncarine F is omitted or removed when providing a *hamelia patens* extract according to the disclosure, the remaining components of the listing remaining present. In some embodiments, all ursolic acid is omitted or removed when providing a *hamelia patens* extract according to the disclosure, the remaining components of the listing remaining present. As a non-limiting example, in some embodiments, all flavones, all rutin, and ephedrine are removed or omitted, the remaining components of the listing remaining present in a *hamelia patens* extract according to this disclosure; however, any one or combination including more than one material in the listing may be removed or omitted. A combination, including a *hamelia patens* extract, according to the disclosure and useful in accordance with providing compositions according to some embodiments of this disclosure may thus contain any number between about one and about all of the foregoing materials in the listing, in any combination, each, when present, being independently present in any amount within the ranges specified above.

For some embodiments of the disclosure in which it is intended that a *hamelia patens* extract be contacted with mammalian skin, the extract is present in combination with other materials, of which petrolatum is one non-limiting example. In some embodiments a *hamelia patens* extract (including those described above which omit one or more than one materials from said listing) is present as a component of a mixture comprising an effective amount of an pharmaceutically acceptable carrier, which in some embodiments comprises a lotion, skin crème, or salve. For these embodiments, "pharmaceutically-acceptable carrier" is used in its ordinary sense relative to the different embodiments herein, generally including pharmaceutically-acceptable, non-toxic diluents or vehicles useful in formulation of pharmaceutical compositions for topical, oral, or basal layer injection to human or animal subjects. Pharmaceutically-acceptable carriers can include, without limitation, one or more than one materials selected from the group consisting of buffering agents, solubilizing agents, stabilizing agents, liquids such as water, saline solution, glycerol and ethanol. Such carriers enable a pharmaceutical composition to be formulated as tablets, pills, dragees, capsules, liquids, gels, syrups, slurries, suspensions, emulsions, and the like for ingestion, injection, or topical application to mammalian skin. A discussion of pharmaceutically-acceptable carriers is available in Remington's Pharmaceutical Sciences (Mack Pub. Co., N.J. 1991).

Only effective amounts of *hamelia patens* extracts are needed to prevent or treat skin conditions such as pre-cancerous lesions, keratotic lesions, radiation-induced burns and other indications recited herein. Topical application to affected skin sites is accomplished in some embodiments by combination of the *hamelia patens* extract with a carrier, and particularly a carrier in which compounds present in the *hamelia patens* extract are soluble per se or are effectively solubilized (e.g., as a solution, suspension, emulsion, or microemulsion), and contacting such combinations to mammalian skin. It is desirable that the carrier be inert in the sense of not bringing about a deactivation, reaction or detrimental chemical change of any components present in a *hamelia patens* extract chosen to be present in the formulation, and in the sense of the carrier not bringing about any adverse effect on skin to which it is applied.

Thus, in some embodiments, suitable carriers of or for a *hamelia patens* extract are those which are pharmaceutically acceptable. Within this class are included water, water-based carriers, alcohols, alcohol-based carriers, oils, and oil-based carriers, mineral oil and petrolatum-based carriers chosen for their ability to dissolve or disperse components present in the

*hamelia patens* extract at concentrations suitable for use in therapeutic treatment of mammalian skin. In some embodiments, relatively low concentrations of *hamelia patens* extract or any of its selected components in a combination according to the disclosure may be employed for instances in which more frequent topical application is undertaken, versus the frequency of application of a composition according to the disclosure in which the *hamelia patens* extract or any of its selected components are present in relatively higher amounts. In some embodiments a composition that is intended to be topically applied is formulated to contain at least about 0.25% and up to about 25% by weight based on the total weight of the composition of crystalline *hamelia patens* extract, and accordingly carriers can be chosen which can solubilize or disperse the components of the crystalline extract at such concentrations. In some embodiments, crystalline *hamelia patens* extract is present in a composition according to the disclosure in any amount between about 0.01% to about 30% by weight based on the total weight of the composition, including all percentages and ranges of percentages therebetween. In some embodiments a composition according to the disclosure contains about 10% by weight total crystalline *hamelia patens* extract.

While the carrier for extract of *hamelia patens* can consist of or comprise a relatively simple solvent or dispersant such as oils, the carrier may comprise materials that make a composition according to this disclosure more conducive to topical application, and particularly carriers which aid in percutaneous delivery and penetration of at least one in some embodiments, and in other embodiments a plurality of components of *hamelia patens* extract into dermal lipid layers. Many such compositions are known in the art, and can take the form of lotions, creams, gels or even solid compositions (e.g., stick-form preparations). Typical compositions include lotions containing water and/or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a crème rather than a lotion, or into gels, or into solid sticks by utilization of different proportions of the ingredients and/or by inclusion of thickening agents such as gums or other forms of hydrophilic colloids. Such compositions are within the class of those comprising pharmaceutically-acceptable carriers. In some embodiments those most preferred for skin are those carriers which are fat-soluble, i.e., those which can effectively penetrate skin layers and deliver the active *hamelia patens* extract or one or a plurality of its components to the lipid-rich layers of the skin. In addition, a *hamelia patens* extract according to the disclosure may be applied using a time-release patch, as are used in hormone delivery, nicotine patches, anti-acne patches, and the like. Crèmes, aqueous solutions, pastes, powders, etc. are all suitable delivery vehicles for an extract of *hamelia patens* or one or more of its components to mammalian skin, which includes human skin.

Thus, a *hamelia patens* extract of the present disclosure (which term includes crystalline and other extracts, synthetically-assembled or otherwise provided), and alternately any of its components in any number, combination, and quantity as earlier set forth may be present in a wide range of compositions suitable to be applied to skin. In addition, a *hamelia patens* extract according to the present disclosure may be present in combination with surfactants and materials which are used in personal care products, in which the level of *hamelia patens* extract ranges from about 1% to up to about 60% by weight based on the total weight of the composition, including all percentages and ranges of percentages therebetween.

To the extent that other materials present in a composition of the disclosure with the *hamelia patens* extract may form binary active systems, ternary active systems etc., in some embodiments the *hamelia patens* extract or component(s) thereof independently present in any amount may comprise the majority of an anti-keratotic system or it may comprise less than the majority of the anti-keratotic system. Surfactants and other materials which can be used in combination with a *hamelia patens* extract in forming personal care compositions according to this disclosure include without limitation: amphoteric/zwitterionic surfactants; anionic surfactants; nonionic surfactants; cationic surfactants; and optional ingredients, including without limitation those described below.

Amphoteric surfactants suitable for inclusion in a composition according to this disclosure in combination with a *hamelia patens* extract or any one or more than one of its components independently present in any amount within the ranges specified above can broadly be described as surface active agents containing at least one anionic and one cationic group and can act as either acids or bases depending on pH. Some of these compounds are aliphatic derivatives of heterocyclic secondary and tertiary amines in which the aliphatic radical may be straight or branched and wherein one of the aliphatic substituents contains from about 6 to about 20, preferably 8 to 18, carbon atoms and at least one contains an anionic water-solubilizing group, e.g., carboxy, phosphonate, phosphate, sulfonate, sulfate.

Zwitterionic surfactants suitable for inclusion in a composition according to this disclosure in combination with a *hamelia patens* extract or any of its components independently present in any amount specified in the ranges above can be described as surface active agents having a positive and negative charge in the same molecule which molecule is zwitterionic at all pH's. Zwitterionic surfactants are exemplified by the betaines and the sultaines. The zwitterionic compounds generally contain a quaternary ammonium, quaternary phosphonium or a tertiary sulfonium moiety. The cationic atom in the quaternary compound can be part of a heterocyclic ring. In all of these compounds there is at least one aliphatic group, straight chain or branched, containing from about 6 to 20, preferably 8 to 18, carbon atoms and at least one aliphatic substituent containing an anionic water-solubilizing group, e.g., carboxy, sulfonate, sulfate, phosphate or phosphonate.

Examples of amphoteric and zwitterionic surfactants suitable for inclusion in a composition in combination with a *hamelia patens* extract or any of its components independently in any amount specified within the ranges above according to the present disclosure include the alkali metal, alkaline earth metal, ammonium or substituted ammonium salts of alkyl amphocarboxyglycinates and alkylamphocarboxypropionates, alkyl amphodipropionates, alkyl monoacetate, alkyl diacetates, alkylamphoglycinates, and alkyl amphopropionates wherein alkyl represents an alkyl group having from 6 to about 20 carbon atoms. Other suitable surfactants include alkyliminomonoacetates, alkyliminidiacetates, alkyliminopropionates, alkyliminidipropionates, and alkylamphopropylsulfonates having between 12 and 18 carbon atoms, alkyl betaines and alkylamidoalkylene betaines and alkyl sultaines and alkylamidoalkylenehydroxy sulfonates.

Anionic surfactants suitable for inclusion in a composition in combination with a *hamelia patens* extract or any of its components independently present in any amount specified in the ranges above according to the present disclosure are those surfactant compounds which contain a long chain hydrocarbon hydrophobic group in their molecular structure and a hydrophilic group, including salts such as carboxylate, sulfonate, sulfate or phosphate groups. The salts may be sodium, potassium, calcium, magnesium, barium, iron, ammonium and amine salts of such surfactants. Anionic surfactants include the alkali metal, ammonium and alkanol ammonium salts of organic sulfuric reaction products having in their molecular structure an alkyl, or alkaryl group containing from 8 to 22 carbon atoms and a sulfonic or sulfuric acid ester group. Examples of such anionic surfactants include water-soluble salts of alkyl benzene sulfonates having between 8 and 22 carbon atoms in the alkyl group, alkyl ether sulfates having between 8 and 22 carbon atoms in the alkyl group and 2 to 9 moles ethylene oxide in the ether group. Other anionic surfactants include alkylsulfosuccinates, alkyl ethersulfosuccinates, olefin sulfonates, alkyl sarcosinates, alkyl monoglyceride sulfates and ether sulfates, alkyl ether carboxylates, paraffinic sulfonates, mono and di-alkyl phosphate esters and ethoxylated derivatives, acyl methyl taurates, fatty acid soaps, collagen hydrosylate derivatives, sulfoacetates, acyl lactates, aryloxide disulfonates, sulfosucinamides, naphthalene-formaldehyde condensates and the like. Aryl groups generally include one and two rings, alkyl generally includes from 8 to 22 carbon atoms and the ether groups generally range from 1 to 9 moles of ethylene oxide (EO) and/or propylene oxide (PO), preferably EO. Specific anionic surfactants which may be selected include linear alkyl benzene sulfonates, including without limitation those such as decylbenzene sulfonate, undecylbenzene sulfonate, dodecylbenzene sulfonate, tridecylbenzene sulfonate, nonylbenzene sulfate and the sodium, potassium, ammonium, triethanol ammonium and isopropyl ammonium salts thereof.

Nonionic surfactants may also be present in a composition according to the disclosure in combination with a *hamelia patens* extract or any of its components independently present in any amount specified within the ranges above. The nonionic surfactant (s) may be any of the known nonionic surfactants which, as with other surfactants discussed herein, are generally selected on the basis of compatibility, effectiveness and economy and present in a composition according to the disclosure in effective amount to enhance wettability or permeability of mammalian skin when applied thereto or to otherwise beneficially modify activity of components present in a combination provided herein. Examples of useful nonionic surfactants include without limitation condensates of ethylene oxide with a hydrophobic moiety which has an average hydrophilic lipolytic balance (HLB) between about 8 to about 16, and in some embodiments between about 10 and about 13. Nonionic surfactants include the ethoxylated primary or secondary aliphatic alcohols having from about 8 to about 24 carbon atoms, in either straight or branch chain configuration, with from about 2 to about 40, and in some embodiments between about 2 and about 9 moles of ethylene oxide per mole of alcohol. Other suitable nonionic surfactants include the condensation products of from about 6 to about 12 carbon atoms alkyl phenols with about 3 to about 30, and preferably between about 5 to about 14 moles of ethylene oxide.

Many cationic surfactants are known in the art and almost any cationic surfactant having at least one long chain alkyl group of about 10 to 24 carbon atoms is suitable for optional use as a component in a composition which includes a *hamelia patens* extract according to the present disclosure.

Other optional ingredients or additives which may be used in combination with *hamelia patens* extract in formulating compositions according to the present disclosure include pH adjusting chemicals, for example, loweralkanolamines such as monoethanolamine (MEA) and triethanolamine (TEA). Sodium hydroxide solutions may also be utilized as an alkaline pH adjusting agent. The pH adjusting chemicals function to neutralize acidic materials that may be present. Mixtures of more than one pH adjusting chemical can also be utilized.

Phase regulants (well known liquid detergent technology) may also be optionally present in a composition of the disclosure. These can be represented by lower aliphatic alcohols having from 2 to 6 carbon atoms and from 1 to 3 hydroxyl groups, ethers of diethylene glycol and lower aliphatic monoalcohols having from 1 to 4 carbon atoms and the like.

Detergent hydrotropes may also be included in a composition according to the disclosure. Examples of detergent hydrotropes include salts of alkylarylsulfonates having up to 3 carbon atoms in the alkyl group e.g., sodium, potassium, ammonium, and ethanolamine salts of xylene, toluene, ethylbenzene, cumene, and isopropylbenzenesulfonic acids.

Other optional supplemental additives include de-foamers such as high molecular weight aliphatic acids, especially saturated fatty acids and soaps derived from them, dyes and perfumes; fluorescent agents or optical brighteners; suspension stabilizing agents; antioxidants; softening agents; uv-light inhibitors or absorbers; preservatives; polyacids, opacifiers, and bacteriacides.

An inorganic or organic builder may optionally be added in small amounts to a composition according to some embodiments of the disclosure. Examples of inorganic builders include water-soluble alkali metal carbonates, bicarbonates, silicates and crystalline and amorphous alumino-silicates. Examples of organic builders include the alkali metal, alkaline metal, ammonium and substituted ammonium polyacetates, carboxylates, polycarboxylates, polyacetyl carboxylates and polyhydroxy sulfonates.

*Hamelia patens* extracts of the present disclosure are useful in providing compositions which contain materials typically known to and used by those skilled in the art of formulation as being useful in formulating skin-care compositions, shampoos and other products, particularly, but not limited, to products intended for topical application. For purposes of this disclosure, the words "materials typically known to and used by those skilled in the art of formulation" means one, or any combination comprising more than one of the materials selected from the group consisting of: fatty acids, alkyl sulfates, ethanolamines, amine oxides, alkali carbonates, water, ethanol, isopropanol, pine oil, sodium chloride, sodium silicate, polymers, alcohol alkoxylates, zeolites, aloe, vitamins, emu oil, anti-oxidants, carotenoids, terpenoids, flavonoids, hormones, perborate salts, alkali sulfates, enzymes, hydrotropes, dyes, fragrances, preservatives, brighteners, builders, polyacrylates, essential oils, alkali hydroxides, ether sulfates, alkylphenol ethoxylates, fatty acid amides, alpha olefin sulfonates, paraffin sulfonates, betaines, chelating agents, tallowamine ethoxylates, polyetheramine ethoxylates, ethylene oxide/propylene oxide block copolymers, alcohol ethylene oxide/propylene oxide low foam surfactants, methyl ester sulfonates, alkyl polysaccharides, N-methyl glucamides, alkylated sulfonate diphenyl oxide, and water soluble alkylbenzene sulfonates or alkyltoluene sulfonates, each present when selected in conventionally-used amounts.

In one embodiment, any *hamelia patens* extract of the present disclosure may be present in facial and body cleansing compositions. These cleansing compositions may also comprise a fatty acid soap together with other non-soap surfactants, such as mild synthetic surfactants. Body and facial cleaning compositions may also generally include a moisturizer or emollient and polymeric skin feel and mildness aids. The compositions may further optionally include thickeners (e.g., magnesium aluminum silicate, carbopol), conditioners, water soluble polymers (e.g., carboxymethyl cellulose), dyes, hydrotropes brighteners, perfumes, and germicides.

In some embodiments, any extract of *hamelia patens* of the present disclosure may be present in a shampoo. The shampoo composition may also comprise one or more other surfactants, optionally a compound considered useful for treating dandruff, such as selenium sulfide, a suspending agent, an amide, nonionic polymer material for aiding in dispersing particles, nonvolatile silicone fluid, and a variety of other nonessential components suitable for rendering the composition more formulatable, such as preservatives, viscosity modifiers, pH adjusting chemicals, perfumes, and dyes.

In other embodiments, any *hamelia patens* extract of the present disclosure may be present in a light-duty detergent composition. The light duty detergent composition may further include one or more other surfactants, opacifiers (e.g. ethylene glycol di-stearate), thickeners (e.g. guar gum), anti-microbial agents, anti-tarnish agents, heavy metal chelators (e.g. EDTA), perfumes and dyes.

In further embodiments, any *hamelia patens* extract of the present disclosure may be present in a heavy-duty detergent composition. The heavy duty detergent composition may also include one or more other surfactants, an electrolyte (i.e. water soluble salt), enzymes with or without stabilizers such as calcium ion, boric acid, propylene glycol and/or short chain carboxylic acids, and conventional alkaline detergency builders.

In yet other embodiments, any *hamelia patens* extract of the disclosure may be present in a conditioner composition that comprises alkylamine compounds.

In other embodiments, any *hamelia patens* extract of the present disclosure may be present in a cosmetic composition, such as lipstick, and including lip balms. The cosmetic composition may further include at least one polymer thickening agent, one or more chemical preservatives or water activity depressants to prevent microbial spoilage, a sun-screening agent such as p-aminobenzoic acid, cinnamic acid derivatives, and a vehicle. The vehicle can include any diluent, dispersant or carrier useful in ensuring an even distribution of the composition when applied to skin and may include water, an emollient such as an alcohol or oil, a propellant for example, trichloromethane, carbon dioxide or nitrous oxide, a humectant, and a powder such as chalk, talc, and starch.

From the foregoing it is evident that the disclosure provides compositions in which a *hamelia patens* extract is present. These compositions and others evident from this disclosure are efficacious in a wide range of therapeutic and cosmetic end uses.

One such end use for a composition comprising a *hamelia patens* extract according to the disclosure is in providing components present in *hamelia patens* extract to be present on clothing, such as by employing a laundry detergent formulation according to the disclosure, which can provide components of the *hamelia patens* extract to affected areas including the torso and extremities of skin areas.

Another end use for a composition comprising a *hamelia patens* extract according to the disclosure is in providing dental pastes, dentrifices, oral ointments, colloidal suspensions and gels containing *hamelia patens* extract which can be applied to inflamed, lacerated, or other affected or symptomatic areas on the gums for relief from aphthous ulceration, gum papillae, mouth lesions, tissue flaps, wounds, and angular chelitis of the mouth and/or lips.

Another end use for a composition comprising a *hamelia patens* extract according to the disclosure is in the field of ophthalmology. Extracts and compositions according to the disclosure are useful in treating cataracts, pteregium, conjunctival pterygium, photokeratitis, keratopathy and other conditions caused by solar radiation. Medications that can be adapted to use for the areas surrounding the eye in order to minimize or avoid irritation when treating skin adjacent to eye lids that have solar damage. For such embodiments a *hamelia patens* extract is put up in a vehicle that is opthamologically-acceptable, including the presence of appropriate buffers and absence of materials that tend to cause irritation or inflammation.

Another end use for a composition comprising a *hamelia patens* extract according to this disclosure is in the field of treatment of skin conditions, including cancer-related skin conditions, including superficial basal cell carcinomae, squamous cell carcinomae, malignant melanoma, Kaposi's sarcoma, cutaneous lymphomae, and Merkel cell carcinomae. In some embodiments, a salve, crème, ointment, emulsion, or lotion containing an extract of *hamelia patens* according to the disclosure may be applied topically to an affected area, with gentle rubbing. In some embodiments, a salve, crème, ointment, or lotion including a *hamelia patens* extract according to the disclosure is applied once daily to such an affected area. In other embodiments, a salve, crème, ointment, or lotion including a *hamelia patens* extract according to the disclosure is applied twice daily to such an affected area. In another embodiment, a salve, crème, ointment, or lotion including a *hamelia patens* extract according to the disclosure is applied thrice daily to such an affected area. In another embodiment, a salve, crème, ointment, or lotion including a *hamelia patens* extract according to the disclosure is applied four times daily to such an affected area. In other embodiments, a salve, crème, ointment, or lotion including a *hamelia patens* extract according to the disclosure is applied more than four times daily to such an affected area.

Another end use for a *hamelia patens* extract according to this disclosure is in the field of treatment of pre-cancerous skin conditions, by topical application of *hamelia patens* extract. In some embodiments, a salve, crème, ointment, or lotion including *hamelia patens* extract according to the disclosure is applied to such a selected area of mammalian skin. A salve, crème, ointment, or lotion including *hamelia patens* extract according to the disclosure can be applied to mammalian skin on a maintenance schedule once or more times daily to prevent recurrence of cancerous lesions in individuals with extensive sun damage, history of multiple skin cancers and pre-cancerous growths, and areas following Moh's surgery for multi-centric lesions.

Compositions according to the disclosure comprising an extract of *hamelia patens* intended for topical application to skin in some embodiments include additional substances for enhancing transdermal absorption, including without limitation phosphatidyl cholines such as lecithin, water, alcohols, glyceryl ester oils, and dimethylsulfoxide, present in effective transdermal absorption-enhancing amounts. In some embodiments, a salve, crème, ointment, or lotion including an extract of *hamelia patens* according to the disclosure is applied once daily to an area of skin showing no symptoms of any disorder, in a preventative capacity. In other embodiments, a salve, crème, ointment, or lotion including an extract of *hamelia patens* according to the disclosure is applied once daily to a pre-cancerous lesion. In other embodiments, a salve, crème, ointment, or lotion including an extract of *hamelia patens* according to the disclosure is applied at least twice daily to a pre-cancerous lesion or a normal area present on skin. A normal area present on skin is one which has no evidence of any abnormal condition as viewed by the naked eye. In other embodiments, a salve, crème, ointment, or lotion including an extract of *hamelia patens* according to the disclosure is applied at least thrice daily to a pre-cancerous lesion or a normal area present on skin. In other embodiments, a salve, crème, ointment, or lotion including an extract of *hamelia patens* according to the disclosure is applied at least four times daily to a pre-cancerous lesion or a normal area present on skin. In other embodiments, a salve, crème, ointment, or lotion including an extract of *hamelia patens* according to the disclosure is applied more than four times daily to a pre-cancerous lesion or a normal area present on skin. In some embodiments, a salve, crème, ointment, or lotion including an extract of *hamelia patens* according to the disclosure is applied twice daily to a pre-cancerous lesion or a normal area present on skin for about two weeks. The dry, scaly, whitish to localized reddening area of solar keratosis is replaced by new pink skin growth. In some instances a keratotic area may re-cur. In such instances the topical application of a composition comprising an extract of, or components of an extract of, *hamelia patens* extract present in a vehicle according to the disclosure is repeated, as no detrimental effects have been observed in so doing, the *hamelia patens* extract being benign and innocuous.

Other end uses for an extract of *hamelia patens* according to this disclosure are in the field of enhancing healing of skin that is worn or damaged from various environmental and other effects (including artificial "tanning beds" present in tanning salons) by topical application of a salve, crème, ointment, or lotion including an extract of *hamelia patens* according to the disclosure, also including reversal of skin aging, skin wrinkling, alleviating symptoms induced by external beam irradiation such as resulting from treating cancers with radiation, anti-fungal effect on skin, treatment of external hemorrhoids, treatment of sunburns and other ultraviolet light-induced skin conditions, treatment of autoimmune disorders including without limitation psoriasis, eczema, chronic skin ulceration, chronic dermatitis, animal bites including cat bites, venous stasis ulceration, cuts, insect bites, skin inflammation, skin rashes, diaper rash, and rosacea.

Other end uses for an extract of *hamelia patens* according to this disclosure are in the field of internal medicine, wherein a crystalline extract of hamelia or alternatively components present in *hamelia patens* extract are administered systemically, such as by an oral preparation or by injection. In one embodiment a composition containing components of *hamelia patens* extract is administered orally in an effective amount to exert anti-inflammatory and/or anti-neoplastic effects on epithelial layers of the esophagus, which is of benefit for cases of inflammations associated with esophageal reflux, esophageal ulceration, and carcinogenic exposures. Moreover, the present disclosure provides nasal spray or drops useful for treatment of allergic rhinitis, by incorporation of a *hamelia patens* extract according to the disclosure into a conventional nasal spray or nasal drop formulation at any amount of between about 0.05% and about 20% by weight based on the total weight of the composition, including all percentages and ranges of percentages therebetween.

In another embodiment, a salve, crème, ointment, or lotion containing a *hamelia patens* extract according to the disclosure is also applied to skin following Mohs surgery for invasive skin malignancies.

The present disclosure provides eye drops useful for administration into the eyes, by incorporation of a *hamelia patens* extract according to the disclosure into a conventional isotonic eyedrop formulation at any amount of between about 0.05% and about 5% by weight based on the total weight of the composition, including all percentages and ranges of percentages therebetween. Such eyedrop formulations include the presence of known buffers, to control pH to be at a level that is opthamologically-acceptable.

Below are set forth several examples which shall be interpreted as being exemplary of various embodiments of this disclosure and shall not be construed as delimitive thereof in any way.

EXAMPLE I

Petrolatum Extract of *Hamelia patens*

A one-liter volume of cut and cleaned leaves of *hamelia patens* are compressed and combined with about 125 ml of petrolatum, the mixture being heated to about 65 degrees centigrade for about 10 minutes. The leafy material is mechanically separated from the petrolatum, which is optionally filtered, to afford a petrolatum-borne extract of the plant *hamelia patens*.

EXAMPLE II

Aqueous Alcohol Extract of *Hamelia patens*

500 grams of ground *Hamelia Patens* leaves are combined with 500 ml of a solvent mixture that contains 10% by volume of ethanol in water. The liquid is maintained at room temperature for 30 minutes with occasional stirring of the leaves and solvent. The resulting solution is centrifuged to remove solids and filtered to provide a liquid extract of *hamelia patens* in solution.

EXAMPLE III

Crystalline Extract of *Hamelia patens*

The liquid extract provided in Example II is placed in a vacuum still, heated to fifty degrees centigrade, and subjected to reduced pressure of 300 torr with a slow sweep of nitrogen gas being admitted over the liquid to enhance removal of solvent, the pressure being maintained at 300 torr. Once the solvent has been removed, a crystalline extract of *hamelia patens* remains. This extract is optionally purified via re-crystallization using an ethanol-water mixture.

EXAMPLE IV

Lotion

Five grams of the crystalline extract provided in Example III were placed in a 150 ml beaker. Ninety five grams of Vaseline® moisture locking lotion (unfragranced) were subsequently added to the beaker, and the contents mixed by mechanical means until the extract was substantially evenly dispersed within the lotion to provide a lotion containing 5% of an extract of the plant *hamelia patens*.

EXAMPLE V

Vitamin-fortified Lotion

To forty five grams of the Lotion of example V placed in a 100 ml beaker are added five grams of Vitamin E oil and the beaker contents mixed until at least substantially uniform to provide a Vitamin-fortified lotion.

EXAMPLE VI

Lotion Concentrate

Fifty grams of the crystalline extract provided in Example III were placed in a 150 ml beaker. Fifty grams of Vaseline® moisture locking lotion (unfragranced) were subsequently added to the beaker, and the contents mixed by mechanical means until the extract was substantially evenly dispersed within the lotion to provide a lotion containing 50% of an extract of the plant *hamelia patens*. This lotion may be used as a lotion concentrate suitable as a base stock from which other lotions may be produced.

EXAMPLE VII

Laundry Detergent

A conventional particulate laundry detergent (CHEER® detergent) is disposed on a moving web which may be a conveyor belt and a spray nozzle is disposed above the moving particulate laundry detergent product. The spray nozzle is fed by a solution comprising the extract of Example II, which is sprayed onto the moving detergent powder in a concentration and rate sufficient to provide a laundry detergent comprising an extract of the plant *hamelia patens* at about 1% by weight.

EXAMPLE VIII

Laundry Detergent

A conventional particulate laundry detergent (CHEER® detergent) is disposed on a moving web which may be a conveyor belt and a spray nozzle is disposed above the moving particulate laundry detergent product. The spray nozzle is fed by a solution comprising the extract of Example II, which is sprayed onto the moving detergent powder in a concentration and rate sufficient to provide a laundry detergent comprising an extract of the plant *hamelia patens* at about 10% by weight. This product may be used as is, or used as a concentrate from which other detergents may be produced by blending.

EXAMPLE IX

Salve Containing *Hamelia patens*

To 95 grams of a petrolatum-based extract of the plant *hamelia patens* prepared according to example I, are added five grams of DMSO and 0.5 grams of soy lecithin. The mixture is blended until at least substantially uniform to provide a salve having enhanced transdermal mobility.

EXAMPLE X

Hand Soap

Five grams of the crystalline extract of *hamelia patens* extract according to example III are placed in a 150 ml beaker and blended with ninety five grams of SOFTSOAP® Elementals (Colgate-Palmolive) until at least substantially-homogeneous.

EXAMPLE XI

Injectable Solution

Five grams of purified extract of the *hamelia patens* plant according to example III are combined with 95 grams of a 0.9% (wt.) saline solution. After mixing, the composition is sterilized and put up into ampoules in the usual manner. This solution may be injected into the basal layer of the dermis at any selected location, including into the base of any form of skin cancer, pre-cancerous lesion, isolated and/or skin lesions or growths.

EXAMPLE XII

Dental Paste

| | |
|---|---|
| abrasive | 40% (wt.) |
| glycerol | 20% |
| sorbitol | 25% |
| propylene glycol | 3.0% |
| hydroxyethyl cellulose | 1.0% |
| sodium lauryl sulfate | 1.0% |
| methyl p-hydroxybenzoate | 0.1% |
| saccharin sodium | 1.0% |
| flavor | 0.9% |
| alkali metal halide | 0.5% |
| crystalline extract from to example III | 7.5% |

The above ingredients are combined in the usual manner to provide a dental paste.

EXAMPLE XIII

Oil in Water Emulsion

| | |
|---|---|
| fatty alcohols (50/50 mix C16 + C18) | 15 grams |
| mineral oil | 10 grams |
| petrolatum | 3 grams |
| PEG-15 (oleyl.cetyl alc.) | 5 grams |
| water | 67 grams |
| crystalline extract from to example III | 7.5 grams |

EXAMPLE XIV

Treatment for Solar Keratosis

A 70 year old man having a history of multiple skin cancers excised from his hands in the past, presented with multiple solar keratosis lesions on the back of both hands. The affected areas on this man's hands were treated twice daily with a petroleum jelly extract according to example I. After a three-week period, the lesions had essentially disappeared. Preventive treatment with the petrolatum extract has kept the lesions from re-appearing for over a year of repeated prophylactic treatment. The treatment has shown no adverse reactions nor any indications of toxicity.

EXAMPLE XV

Treatment for Solar Keratosis

Three men in their eight decade of life each having multiple solar keratosis lesions present on their forearms were each treated twice daily by application of a petroleum jelly extract according to example I to the affected areas for a three-week period, after which the lesions had essentially disappeared, with only faint traces of the original lesions remaining. The treatment showed no adverse reactions or indications of toxicity.

In addition, a *hamelia patens* extract also has anti-microbial, anti-bacterial, anti-inflammatory, anti-septic, and wound healing promoting properties. It is further anticipated by this disclosure that an extract of *hamelia patens* has anti-prion activity and anti-viral activity and a composition as described herein is accordingly useful for treating conditions such as warts, shingles, herpes I, herpes II, human papilloma virus (HPV), and other viruses by topical application, injection, oral administration, or ocular administration. Accordingly, extracts and compositions herein described are useful in various forms recognizable by those skilled in this art after reading this specification and the claims appended hereto to treat any disorder involving microbes, inflammation, wounds, and anti-sepsis. In one embodiment, an extract according to example III above is dissolved in ethanol/water mixture to form a composition which is subsequently adsorbed onto a substrate, including without limitation cellulosic substrates, sponges, and SAP polymer substrates. For the cases where a sponge is employed, this provides a convenient means to dispense small amounts of the material to another substrate, such as the hands, or objects such as pens, pencils etc. In one embodiment such a sponge latent with *hamelia patens* extract is contained in an enclosure having a first and second end, each of said ends having a hole disposed therethrough, through which is passed an article such as a toothbrush, pen or pencil, which during its travel through such enclosure is coated with *hamelia patens* extract in sufficient quantity to effectively deactivate or kill microbes present on the surface of such pen or pencil. By extension, such an article is useful for cleaning other implements, including surgical tools.

*Hamelia patens* extracts as provided herein, whether present in crystalline form or liquid form, including oil-based liquids, aqueous liquids or alcohol-water mixtures, etc., as described, are useful in combination with liposomes. Suitable liposomes include those recognized by those skilled in the art as being useful in combination with plant-derived extracts and components present therein as herein described to enhance delivery of such extracts or components to, into, onto, or within the body of a mammalian subject. Liposomes include artificial microscopic vesicles consisting of an aqueous core present and enclosed within either one, or a plurality of phospholipid layers, which structured materials are useful to convey one or any combination including any number greater than one components present in *hamelia patens* extract to target cells or organs of a mammalian subject.

*Hamelia patens* extracts as provided herein, whether present in crystalline form or liquid form, including oil-based liquids, aqueous liquids or alcohol-water mixtures, etc., as described, are useful in combination with nanoparticles. As used herein, a nanoparticle is any particulate form that is less than about one micrometer in at least one dimension, including particulate forms that are less than one micrometer in at least one dimension. Suitable nanoparticles include those recognized by those skilled in the art as being useful in combination with plant extracts and materials present in plant-derived extracts, and include without limitation such nanoparticles as: solid core nanoparticles, hollow core nanoparticles, lipid nanoparticles, PEG nanoparticles, chitosan nanoparticles.

Although this invention has been described and disclosed in relation to various embodiments, modifications, combinations, and alterations of the features of various embodiments disclosed may become apparent to persons of ordinary skill in this art after reading and understanding the teachings of this specification, drawings, and the claims appended hereto. The present disclosure includes subject matter defined by any combinations of any one (or more) of the features, elements, or aspects present described in reference to any embodiment described in this disclosure with one or more feature(s), element(s), or aspect(s) described in relation to any other one (or more) other embodiments described. These combinations include the incorporation of the features and/or aspect(s) of any dependent claim, singly or in combination with features and/or limitations of any one or more than one of the other dependent claims, with features and/or limitations of any one or more than one independent claim(s), with the remaining dependent claims in their original text being read and applied to any independent claim(s) so modified. These combinations also include combination of the features and/or limitations of one or more of the independent claims with features and/or limitations of another one or more than one of the independent claims to arrive at a modified independent claim, with the remaining dependent claims in their original text or alternately as modified per the foregoing, being read and applied to any independent claim(s) so modified.

The invention claimed is:

1. A method for alleviating symptoms induced by external beam irradiation resulting from treating cancers with radiation on the skin of a human subject, which method comprises topically applying a composition containing a *Hamelia patens* extract to an affected skin area of said subject in an effective amount and frequency for alleviation of said symptoms.

2. The method according to claim 1, wherein said composition is in any form selected from the group consisting of: salves, creams, ointments, and lotions.

3. The method according to claim 1 wherein said composition comprises any carrier selected from the group consisting of: water; saline solution, any C1 to C4 alcohol; any glyceryl ester oil; and any mineral oil.

4. The method according to claim 1 wherein said composition comprises a pharmaceutically-acceptable carrier.

5. The method according to claim 1 wherein said extract is an aqueous extract.

6. The method according to claim 1 wherein said extract is a non-aqueous extract.

7. The method according to claim 1 wherein said composition comprises a nanoparticle.

8. The method according to claim 7 wherein said nanoparticle is selected from the group consisting of: solid core nanoparticles, hollow core nanoparticles, lipid nanoparticles, PEG nanoparticles, and chitosan nanoparticles, including mixtures thereof.

9. The method according to claim 1 wherein said composition comprises a liposome.

10. The method according to claim 1 wherein said extract comprises an effective symptom-reducing amount of at least one material selected from the group consisting of: alkaloids, 2-alpha-hydroxyursolic acid, apigenin-7-o-beta d-glucuronide, aricine, catequine, 19-alphahydroxy Asiatic acid, 24-methylenecycloartane-3β-ol, 24-methylcycloart-24-en-3β-ol,2E-3,7,11,15,19-pentamethyl-2-eicosane-1-ol, ephedrine, flavonones, 2'-5-5'-7-tetrahydroxy-7-o-rutinoside, isomaruquine, isopteropodine, maruquine, the methyl ester of maruquine, mitraphylline, narirutin, narirutin (2r), narirutin (2s), oxindole alkaloids, oxindole aricine, palmirine, pigenin-7-o-beta D-glucuronide, pomolic acid, pteropodine, rumberine, rosmarinic acid, rotundic acid, rumberine, rutin, seneciophylline, β-sitosterol, speciophylline, stigmast-4-en-3-3- dione, stigmast-4-en-3-6-dione, stigmasterol, tannins, tormentic acid, uncarine F, and ursolic acid, including any mixtures thereof.

11. The method according to claim 10 wherein said composition comprises all of said materials recited in said group.

12. The method according to claim 10 wherein each material selected to be present in said composition is independently selected to be present in any amount between 0.05% by weight and 30% by weight based on the total weight of said composition.

13. The method according to claim 1 wherein said symptoms include at least one symptom selected from the group consisting of: chronic skin ulceration, chronic dermatitis, skin inflammation, and skin rashes.

14. A method for alleviating symptoms induced by external beam irradiation resulting from treating cancers with radiation on the skin of a human subject, which method comprises topically applying a composition containing a *Hamelia patens* extract to an affected skin area of said subject.

15. The method according to claim 14, wherein said composition is in any form selected from the group consisting of: salves, creams, ointments, and lotions.

16. The method according to claim 14 wherein said composition comprises any carrier selected from the group consisting of: water; saline solution, any C1 to C4 alcohol; any glyceryl ester oil; and any mineral oil.

17. The method according to claim 14 wherein said composition comprises a pharmaceutically-acceptable carrier.

18. The method according to claim 14 wherein said extract is an aqueous extract.

19. The method according to claim 14 wherein said extract is a non-aqueous extract.

20. The method according to claim 14 wherein said symptoms include at least one symptom selected from the group consisting of: chronic skin ulceration, chronic dermatitis, skin inflammation, and skin rashes.

* * * * *